(12) United States Patent
Citterio

(10) Patent No.: US 7,284,552 B2
(45) Date of Patent: Oct. 23, 2007

(54) INHALER DEVICE

(76) Inventor: Mauro Citterio, Via I Maggio, 8, 23875 Osnago (Lecco) (IT)

( * ) Notice: Subject to any disclaimer, the term of this patent is extended or adjusted under 35 U.S.C. 154(b) by 983 days.

(21) Appl. No.: 10/173,996

(22) Filed: Jun. 18, 2002

(65) Prior Publication Data

US 2003/0000523 A1    Jan. 2, 2003

(30) Foreign Application Priority Data

Jun. 28, 2001   (IT) .......................... MI20010357 U

(51) Int. Cl.
*A61M 15/00* (2006.01)
(52) U.S. Cl. .............................. 128/203.21; 128/203.15
(58) Field of Classification Search .......... 128/203.15, 128/203.18, 203.19, 203.21, 204.12, 207.18, 128/206.11, 200.23
See application file for complete search history.

(56) References Cited

U.S. PATENT DOCUMENTS

| | | | | | |
|---|---|---|---|---|---|
| 3,971,377 | A | * | 7/1976 | Damani | 128/200.17 |
| 4,884,565 | A | * | 12/1989 | Cocozza | 128/203.21 |
| 5,349,947 | A | * | 9/1994 | Newhouse et al. | 128/203.21 |
| 5,715,811 | A | * | 2/1998 | Ohki et al. | 128/203.21 |
| 6,378,519 | B1 | * | 4/2002 | Davies et al. | 128/203.21 |
| 6,732,732 | B2 | * | 5/2004 | Edwards et al. | 128/203.21 |
| 7,025,059 | B2 | * | 4/2006 | Pera | 128/203.21 |

* cited by examiner

*Primary Examiner*—Teena Mitchell
(74) *Attorney, Agent, or Firm*—Hedman & Costigan PC; James V. Costigan

(57) ABSTRACT

An inhaler device comprises an inhaler body defining a recess for a capsule holding herein a substance to be inhaled, and a nosepiece communicating with the capsule, and a perforating element coupled to the inhaler body and provided for perforating the capsule for allowing an outside air flow to be mixed with the capsule contents and inhaled through the nosepiece.

2 Claims, 3 Drawing Sheets

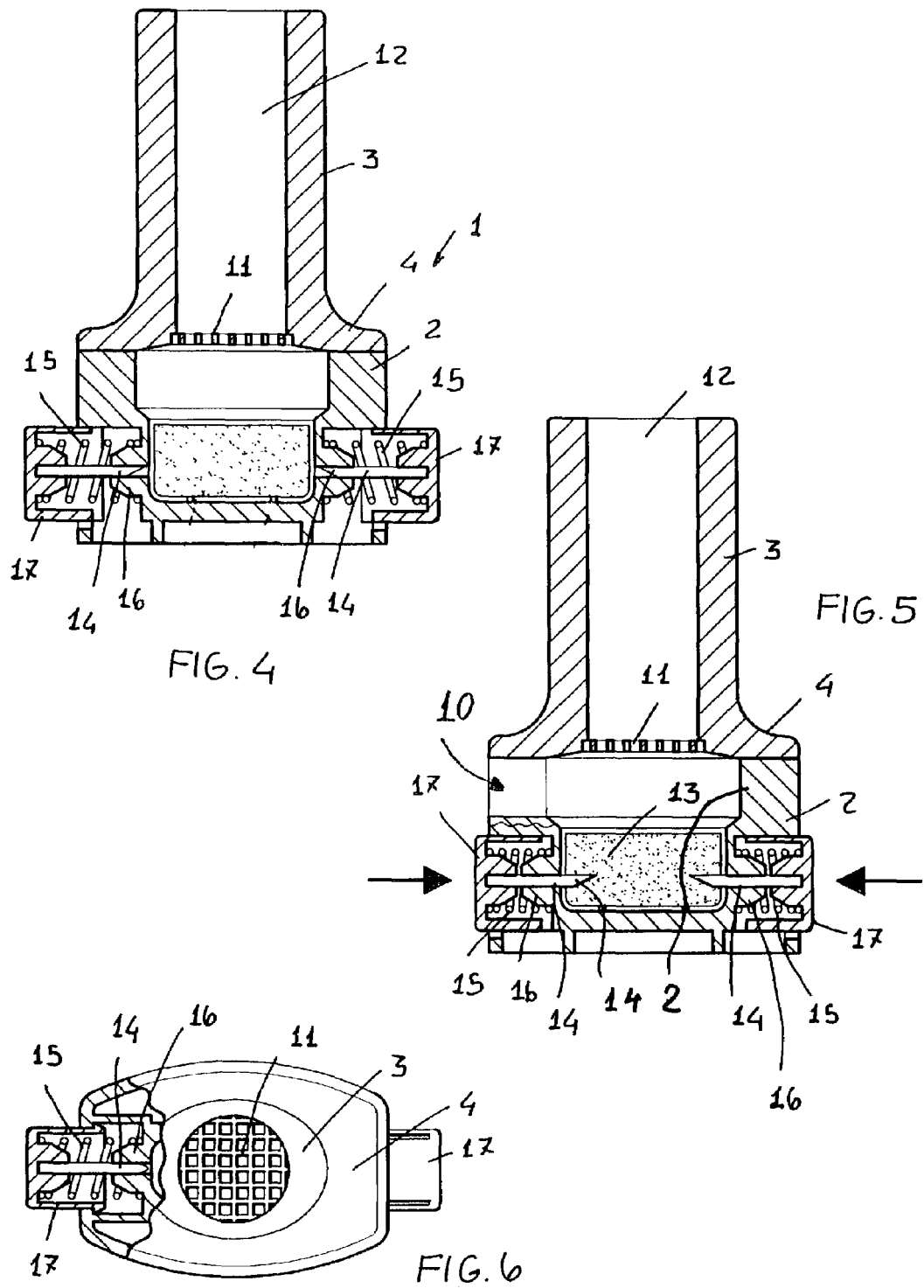

INHALER DEVICE

BACKGROUND OF THE INVENTION

The present invention relates to an inhaler device.

Inhaler devices for inhaling the contents of a capsule, for medical uses, are already known.

Available inhalers, however, are not fully satisfactory from an operating and economic standpoint and, accordingly, they would be susceptible to improvements.

In fact prior inhaler devices are very complex construction-wise, and accordingly very expensive and, moreover, they are affected by frequent operating malfunctions.

SUMMARY OF THE INVENTION

Accordingly, the aim of the present invention is to provide an inhaler device having operating and constructional features improved with respect to those of prior like inhalers.

Within the scope of the above mentioned aim, a main object of the present invention is to provide such an inhaler device which can be easily operated, without any efforts, by a user.

A further object of the present invention is to provide such an inhaler device which allows the capsule held therein to be perfectly perforated, while reducing the possibility of damaging said capsule or clogging the inhaler.

Yet another object of the present invention is to provide such an inhaler device including a small number of component parts.

According to one aspect of the present invention, the above mentioned aim and objects, as well as yet other objects, which will become more apparent hereinafter, are achieved by an inhaler device, comprising an inhaler body, defining a recess for holding therein a capsule containing a substance to be inhaled and a nosepiece communicating with said capsule, characterized in that said inhaler device further comprises perforating means associated with said inhaler body and adapted to perforate said capsule to allow an outside air flow to be mixed with the contents of said capsule for inhalation through said nosepiece.

BRIEF DESCRIPTION OF THE DRAWINGS

Further characteristics and advantages of the present invention will become more apparent hereinafter from the following detailed disclosure of a preferred, though not exclusive, embodiment of the invention, which is illustrated, by way of an indicative, but not limitative example, in the accompanying drawings, where:

FIG. 4 is an elevation cross-sectional view of the inhaler device, shown with a capsule arranged therein, but in a non perforated condition;

FIG. 5 is a view similar to FIG. 4, but illustrating the inhaler device according to the, present invention during the capsule perforating operation; and FIG. 6 is a top plan view, as partially cross-sectioned, of the inhaler device according to the present invention.

DESCRIPTION OF THE PREFERRED EMBODIMENTS

Figure 1:
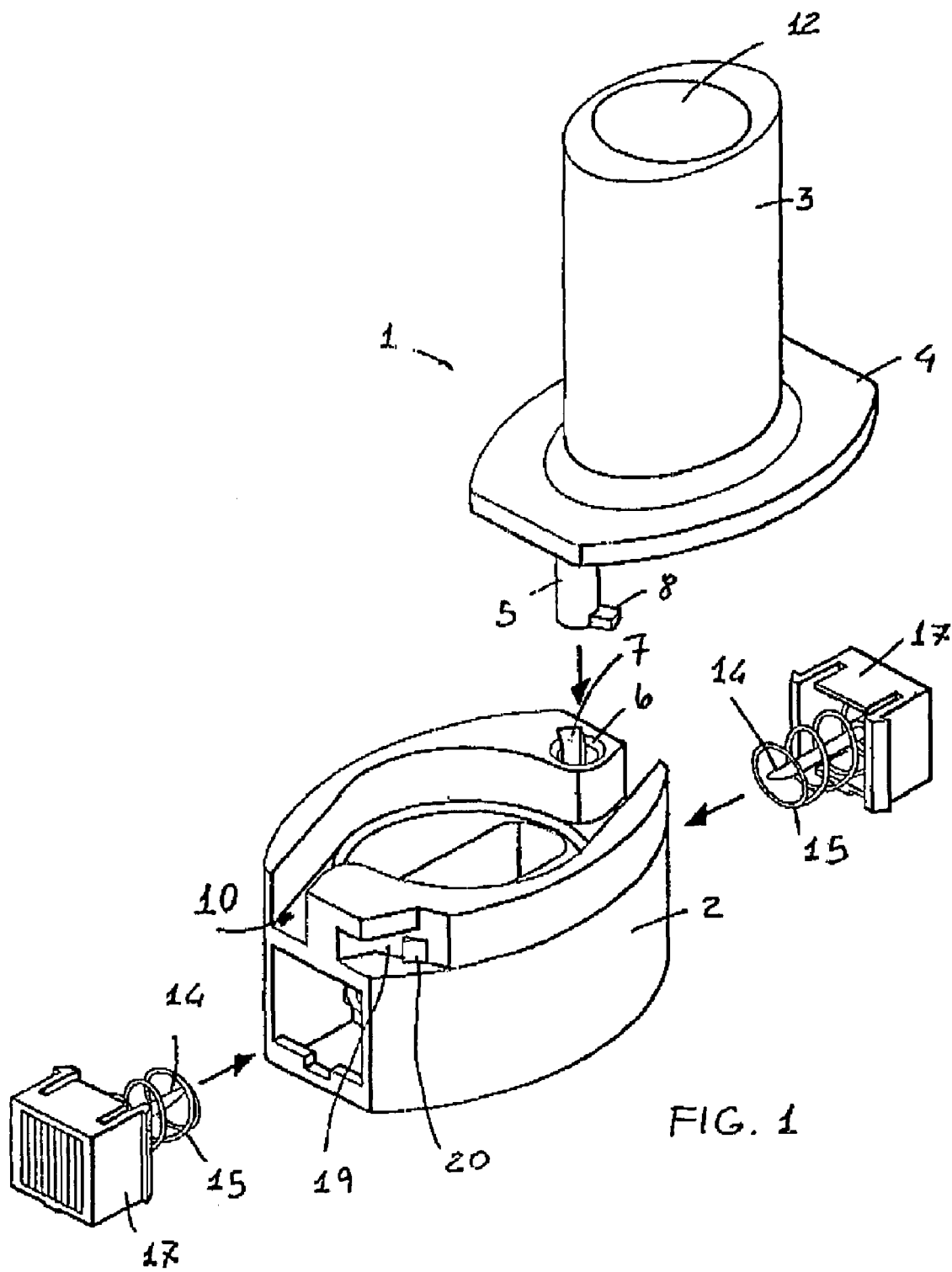
FIG. 1 is an exploded perspective view of the inhaler device according to the invention.

With reference to the number reference of the above mentioned figures, the inhaler device, according to the present invention, which has been generally indicated by the reference number 1, comprises an inhaler nosepiece 3, including a flange 4, having a peg 5 which can be engaged in a corresponding hole 6 formed in an inhaler body 2.

The hole 6 is provided with a longitudinal slot (not shown), that can engage a cross tooth 8 of the peg 5, and a bottom ring-like recess, not specifically shown, in which the tooth 8 can slide.

Thus, it is possible to engage the peg 5 in said hole, by causing the tooth 8 to pass through the slot 7 and, upon achieving the bottom, it is possible to fully rotate the peg 5 in its hole 6, thereby also rotating the inhaler nosepiece 3 with respect to the inhaler body 2.

The inhaler nosepiece 3 can be locked in its closed condition, shown in FIGS. 3-6, by a snap type of locking means, including a hook portion 18 of the flange 4 having a small ridge, not shown, for engaging a corresponding ridge 20 formed inside a latching recess 19, defined in the inhaler body 2.

The inhaler body 2 is moreover provided with a recess for the capsule, said recess being upward opened and communicating with the outside through a perforated plate or grid 11, included in the inhaler nosepiece 3 at said flange 4 and designed for separating the capsule recess 9 from the duct 12 of the nosepiece.

A capsule 13 can be engaged in said recess 9, said capsule being of a per se known type and adapted to be perforated to allow the drug contents held therein to be easily accessed, said perforating operation being performed by any suitable perforating means.

In the disclosed embodiment, the perforating means comprise a pair of perforating needles 14 which can transversely slide as counter-urged by resilient elements comprising, in this embodiment, coil springs 15; each coil spring coaxially encompassing said perforating needle 14 and operating between a respective abutment element 16, rigid with the inhaler body 2, and a hollow push-button element 17.

The perforating needles 14 are similar to hypodermic needles and have a single-side beveled tip, for facilitating said perforating needles 14 in perforating the coating of the capsule 13.

The operation of the inhaler device according to the present invention is as follows.

Figure 2:
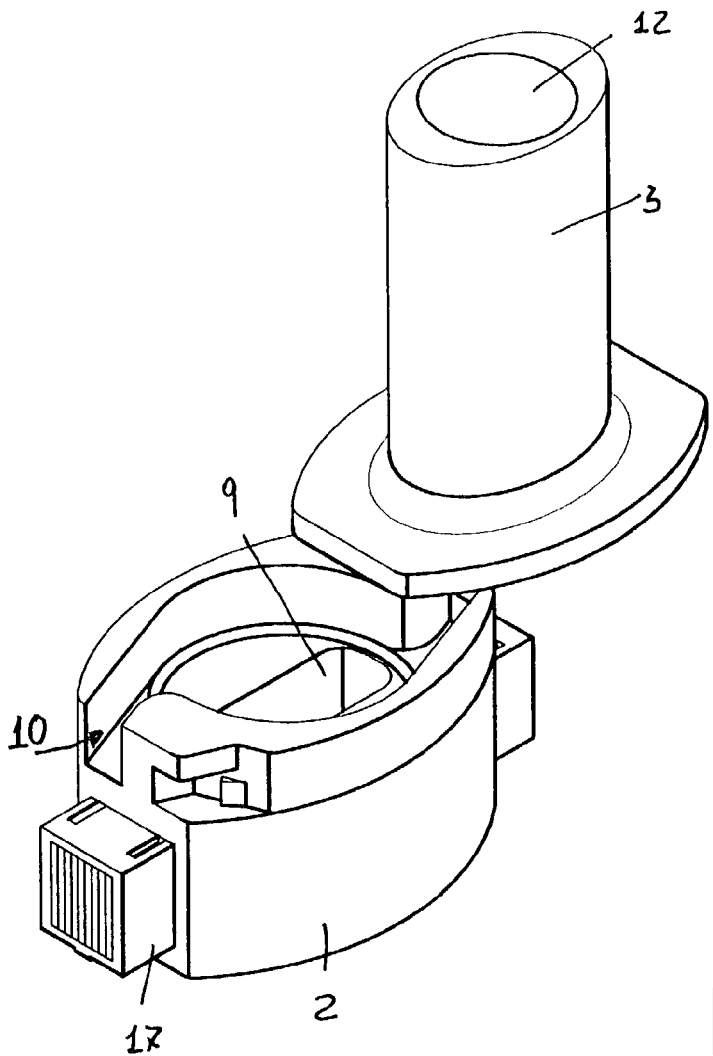
FIG. 2 is a further perspective view of the inhaler device according to the invention shown in an open condition thereof, i.e. in the capsule loading position thereof.
Figure 3:
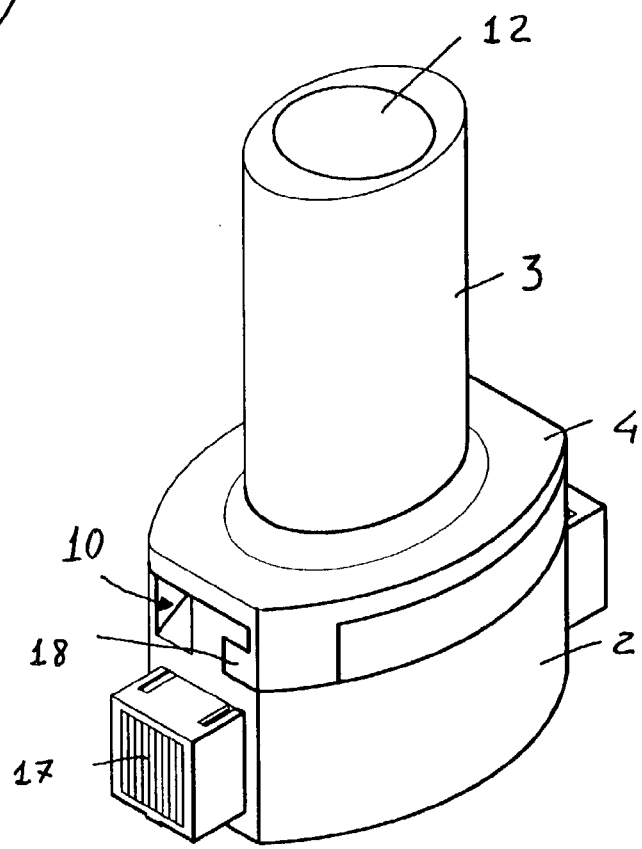
FIG. 3 is a view similar to FIG. 2, but illustrating the inhaler device according to the present invention during the use thereof.

In the open condition, as shown in FIG. 2, a capsule is engaged in the capsule recess 9 and the nosepiece 3 is snap closed on the inhaler body 2.

By pressing the push-button elements 17, the perforating needles 14 will perforate the capsule 13, thereby its contents, usually a fine powder, will be communicated with the capsule recess.

By applying suction on the nosepiece 3, an air flow will be generated which, coming from the outside through the holes 10, will enter the capsule recess, thereby mixing with the capsule contents and, passing through the grid 11 and duct 12, will allow the products to be inhaled.

It has been found that the invention fully achieves the intended aim and objects.

In fact, the invention provides an inhaler device which is very simple construction-wise and can operate in a very satisfactory manner.

A further advantage of the inhaler device according to the invention is the specifically designed configuration of the perforating needles which can be assimilated, as stated, to hypodermic needles.

Since this type of needle presents a very small resistance against perforation and a very accurate operation, it is possible to use needles having a comparatively large diameter, without damaging the capsule, thereby providing a very simple perforating operation.

The use of small number of perforating needles, only two in the preferred embodiment, allows to reduce, the perforated cross section being the same, the contact surface between the needle and capsule, with a consequent reduction of the friction and of the problems affecting the prior inhalers.

In practicing the invention, the used materials, and their size and shapes, can be any, depending on the requirements.

The invention claimed is:

1. A suction operated inhaler device, comprising a stationary bottom inhaler body having an air inlet hole, a latching seat and a latching ridge, said stationary bottom inhaler body further defining a recess for holding therein a capsule containing a substance to be inhaled and a top nosepiece communicating with said capsule, said top nosepiece having a bottom flange and being rotatably coupled to said stationary bottom inhaler body to provide, as said top nosepiece is manually rotated by an inhaler device user, at least two operating conditions including an open condition in which said recess for said capsule can be accessed to engage therein a new capsule or to withdraw therefrom a used capsule, and a closed use condition in which said inhaler device nosepiece can be snap locked by snap locking means, said inhaler device further comprising two opposite perforating needles associated with said inhaler body and adapted to perforate said capsule to allow a contents of said capsule to enter said capsule recess thereby an inhaling suction generated air flow passing through said air inlet hole is mixed with said contents of said capsule for inhaling said contents in said recess through said nosepiece, each perforating needle of said two perforating needles transversely sliding against the biassing of a respective coil spring and operating between an abutment element rigid with said inhaler body and a corresponding operating hollow push button having a push button cavity, each said perforating needle being arranged in said push button cavity of each said hollow push-button and having a contour similar to that of a hypodermic needle, including a single beveled tip, each said respective coil spring substantially fully coaxially encompassing a respective said perforating needle with said hollow pushbutton element in a non operated condition thereof.

2. An inhaler device according to claim 1, wherein said snap locking means comprise a hook portion of said bottom flange or said nosepiece, said bottom flange having a flange ridge engageable with said latching ridge of said inhaler body, said flange comprising a peg having a tooth which can be slidably engaged in a longitudinal slot of a hole formed in said inhaler body, said hole comprising a bottom annular recess in which said tooth can slide, thereby allowing said peg to be rotatively engaged in said hole.

* * * * *